United States Patent [19]
Fukumoto et al.

[11] Patent Number: 5,419,755
[45] Date of Patent: May 30, 1995

[54] WEIGHT BEARING BRACE FOR FEMUR AND HIP JOINT

[76] Inventors: Kazuhito Fukumoto, 33-14, Kengunhonmachi, Kumamoto-shi, Kumamoto, Japan, 862; Hirotoshi Saruwatari, 1317-3, Kajiomachi, Kumamoto-shi, Kumamoto, Japan, 861-55; Shozo Tokuda, 6-27-20, Ohe, Kumamoto-shi, Kumamoto, Japan, 862

[21] Appl. No.: 140,535

[22] Filed: Oct. 25, 1993

[30] Foreign Application Priority Data

May 30, 1992 [JP] Japan ............................ 4-043367 U

[51] Int. Cl.⁶ .................................................. A61F 3/00
[52] U.S. Cl. ........................................ 602/23; 602/26
[58] Field of Search ............... 602/19, 23, 5, 12, 24, 602/26, 16; 128/95.1

[56] References Cited

U.S. PATENT DOCUMENTS

| | | | |
|---|---|---|---|
| 2,558,986 | 7/1951 | Geelert | 602/23 X |
| 2,632,440 | 3/1953 | Hauser et al. | 602/23 X |
| 4,494,534 | 1/1985 | Hutson | 602/23 X |

Primary Examiner—Richard J. Apley
Assistant Examiner—Beverly A. Meindl
Attorney, Agent, or Firm—Cushman, Darby & Cushman

[57] ABSTRACT

A weight bearing brace for a patient having femur or hip joint trouble has an upper socket removably attached to the periphery of an upper part of a thigh; a lower socket removably attached to the periphery of a lower part of the thigh; connectors for connecting the upper and lower sockets to each other, bearing patient's weight, and maintaining a required space between the upper and lower sockets; and a pelvis supporter disposed at an upper end of the upper socket, to substantially receive the weight of the upper half of the patient. The patient with the brace is able to move the hip joint. The pelvis supporter supports a lower part of the pelvis, to directly transfer the weight of the upper half of the patient from the upper socket to the lower socket, thereby avoiding the femur and hip joint from receiving the weight. The brace has a simple structure, is low cost, is easily attached to and detached from a thigh, and allows a knee joint with the brace to move, to smoothly carry out rehabilitation.

6 Claims, 8 Drawing Sheets

WEIGHT BEARING BRACE FOR FEMUR AND HIP JOINT

BACKGROUND OF THE INVENTION

1. Field of the Invention

The present invention relates to a weight bearing brace for supporting a femur and hip joint when treating a patient having femur or hip joint disorder.

2. Description of the Related Art

When a patient has a dislocated, broken, inflamed, or necrotic femur or hip joint, the patient must be treated with the femur and hip joint bearing no weight. For this purpose, a prior art procedure measures the size of the patient along a leg involving the affected part, prepares a support according to the measurements, attaches the support to the leg, and puts a plaster cast around the hip and thigh area of the patient. After one or two months with the plaster cast, the patient gradually practices to walk on the sound leg with crutches.

FIG. 9 shows a brace E according to another prior art device. The brace E has a support R attached along a leg by winding belts B around a thigh, knee, and ankle, so that a sole is spaced away from the ground. The brace has a shoe S to cover the ankle and sole.

The former prior art device that applies a plaster cast around patient's hip and thigh involves intricate processes of measuring patient's lower body, forming a support according to the measurements, and applying the support and a plaster cast to the patient. The plaster cast is broken afterward to start rehabilitation. The plaster cast is not recyclable. With the plaster cast, the patient is unable to move his or her thigh nor walk. As a result, muscles under the plaster cast atrophy, and a long rehabilitation period is required to restore the atrophied muscles after removing the plaster cast. This results in delaying the patient from returning to work.

According to the latter prior art of FIG. 9, the brace E may allow the patient to walk with crutches. The patient, however, must walk with his or her thigh immobilized because a linear support R is fixed to the leg. This results in atrophying the muscles of the immobilized part, and requires a long rehabilitation period. The brace E with the support R, shoe S, and belts B around the thigh, knee, and ankle provides a bulky poor appearance. The brace E forces the patient to endure daily inconveniences. With such a large number of components, the brace E is not easy to apply to a patient and involves many processes and a long time to manufacture to thereby increasing costs.

SUMMARY OF THE INVENTION

An object of the present invention is to provide a weight bearing brace for a patient having femur or hip joint disorder. The brace is easily attached to and detached from the femur area of the patient and requires no measurement of the patient nor fabrication of a plaster cast. The brace has a simple structure, is inexpensive, and provides a good appearance. The brace allows the patient to freely move his or her thigh, hip joint, muscles, knee joint, etc., to spend a normal life, rehabilitate his or her muscles, and return early to work.

In order to accomplish the object, a weight bearing brace (10) for a patient having femur or hip joint disorder according to the present invention has an upper socket (12) removably attached to the periphery of an upper part of a thigh (T), a lower socket (14) removably attached to the periphery of a lower part of the thigh (T), connectors (16) for connecting the upper and lower sockets (12, 14) to each other, bearing patient's weight, and maintaining a required space between the upper and lower sockets (12, 14), and a pelvis supporter (20) disposed at an upper end of the upper socket (12), to substantially support the weight of the upper half of the patient.

The lower socket (14) has an inverted U shape in a plan view. The inner face of the lower socket (14) may have an attaching part (32) to be applied to a condyle area above a knee joint (H).

Each of the connectors (16) may have an adjuster (46) for longitudinally extending and shortening the connector (16).

The lower socket (14) may be rotatably attached to lower ends of the connectors (16).

The brace (10) may employ a positioner (33) fitted around the periphery of a lower part of the thigh (T) with the periphery of the positioner (33) being fastened with the lower socket (14), to firmly position the lower socket (14) with respect to the periphery of the lower part of the thigh (T).

The positioner (33) may be made of an annular rubber or synthetic resin material.

The brace (10) removably attached to the thigh relieves load from the femur, etc., when treating the femur or hip joint of the patient. The pelvis supporter (20) supports a lower part of a pelvis when the upper socket (12) is attached to the upper periphery of the thigh, to allow the hip joint to move. The lower socket (14) is attached to the lower periphery of the thigh to allow a knee joint to move. The weight of the patient is directly transferred from the upper socket (12) to the lower socket (14) and is supported.

The weight bearing brace according to the present invention may be a ready-made product that requires no plaster casting and is applicable for any patient. A patient with the brace is allowed to freely move and rehabilitate thigh muscles and a knee joint, so that the patient may receive sufficient treatments and quickly return to work.

DESCRIPTION OF THE PREFERRED EMBODIMENTS

Figure 1:
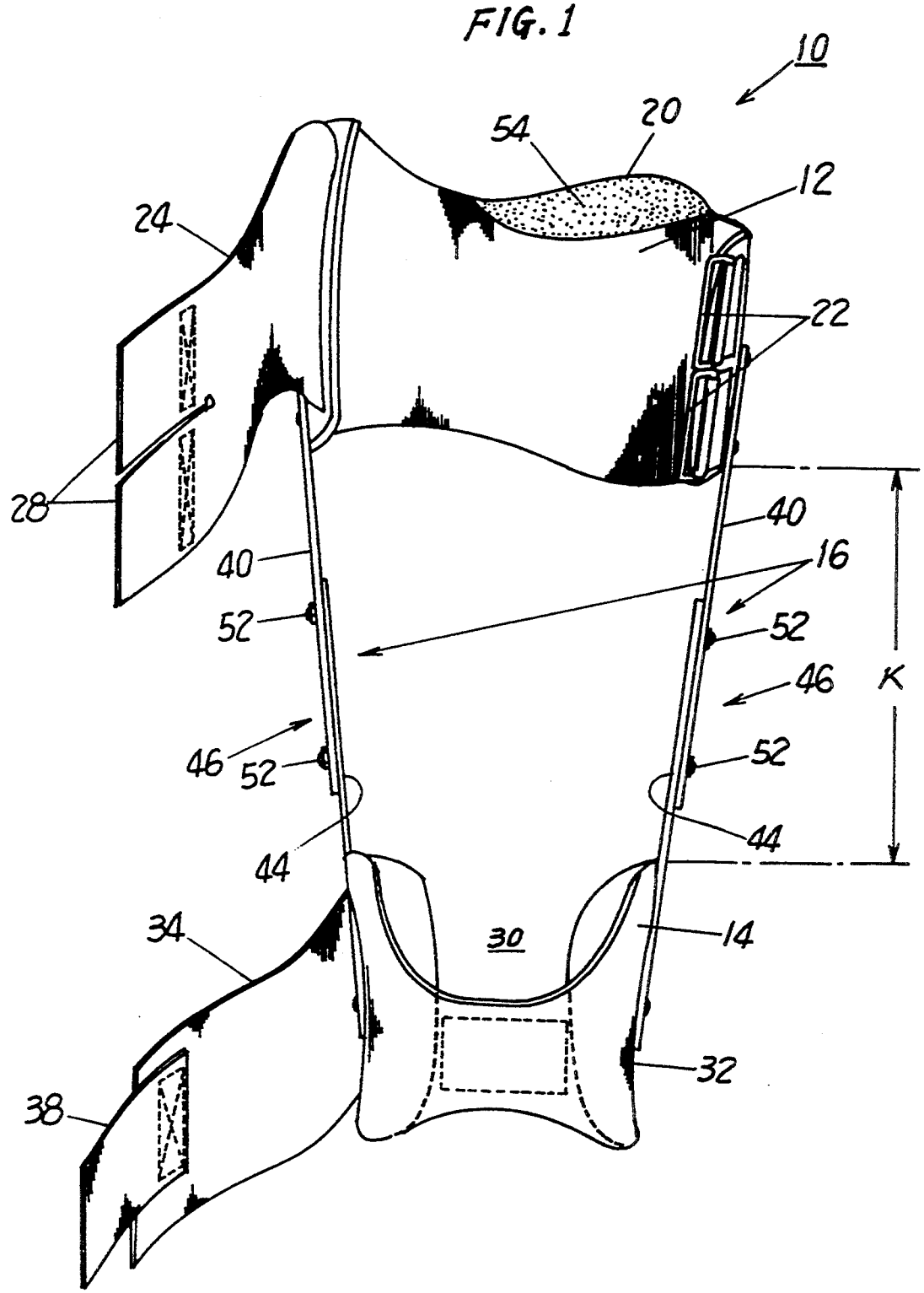
FIG. 1 is a front view showing a weight bearing brace for a thigh bone and hip joint according to an embodiment of the present invention.

A preferred embodiment of the present invention will be explained with reference to the drawings.

FIGS. 1 to 5 show a weight bearing brace 10 for a femur and hip joint according to the embodiment of the present invention. The brace 10 is employed to treat a patient having a dislocated, broken, or inflamed femur or hip joint.

The brace 10 has an upper socket 12 to be removably attached to the periphery of an upper part of a thigh, a lower socket 14 to be removably attached to the periphery of a lower part of the thigh, and connectors 16 for connecting the upper and lower sockets 12 and 14 to each other.

The upper socket 12 is made of hard thin material such as hard synthetic resin or light metal. The upper socket 12 has an opening 18 (FIG. 3) to substantially form a U shape in a plan view, to cover the back and sides of the thigh.

An upper end of the upper socket 12 has a pelvis supporter 20 to be explained later.

Annular stoppers 22 are fixed to an edge of the opening 18 of the upper socket 12. The other edge of the opening 18 has a fastening band 24 made of elastic material. The outer face of the band 24 is rough. Stopper tongues 28 are sewn to an end of the band 24. Each of the tongues 28 has a velvet fastener 26. The upper socket 12 is fitted to the upper periphery of the thigh, the tongues 28 of the band 24 are inserted into the annular stoppers 22, and the leading ends of the tongues 28 are folded so that the velvet fasteners 26 of the tongues 28 are removably attached to the surfaces of the tongues 28.

Similar to the upper socket 12, the lower socket 14 is made of hard thin material such as hard synthetic resin. The lower socket 14 has an inverted U shape in a plan view, to cover the front and sides of the lower periphery of the thigh just above a knee joint. Unlike the upper socket 12, the lower socket 14 has an opening 30 on the back thereof. An attaching part 32 is fixed to the inner face of the lower socket 14, to get in contact with a front part of the thigh just above a knee when the lower socket 14 is worn. The attaching part 32 is made of a rough sheet such as a velvet fastener. The rough sheet is positioned around the part just above the knee joint, to fix the lower socket 14 to the part.

Figure 4:
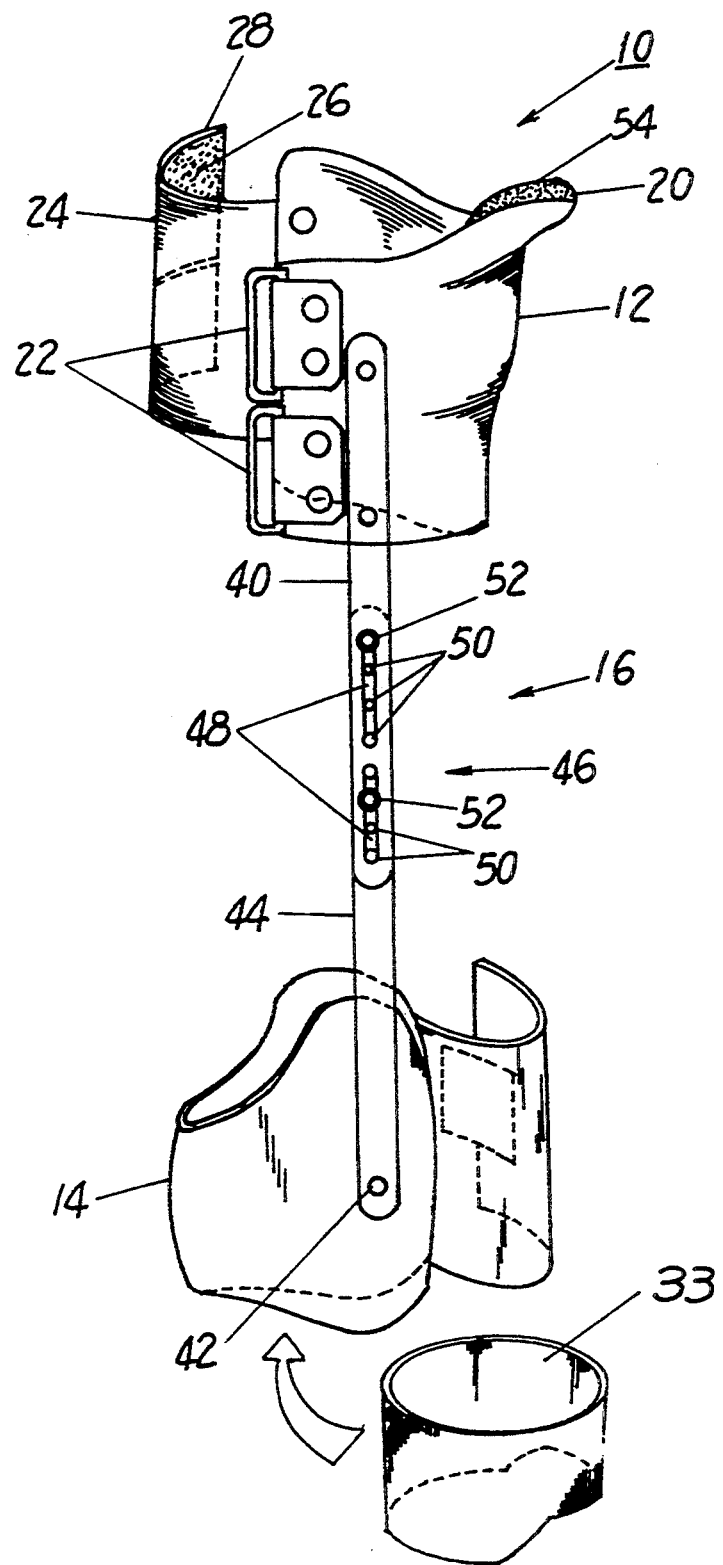
FIG. 4 is a right side view of the brace.

In FIG. 4, a positioner 33 is applied before attaching the lower socket 14. The positioner 33 is an annular member made of nonslip porous material such as "Neoprene" rubber. The positioner 33 is attached to the lower periphery of the thigh before attaching the lower Socket 14 thereto. Once the positioner 33 is surely positioned on the skin of the lower part of the thigh, it will not vertically slip. The lower socket 14 is then attached to the surface of the positioner 33, and the fitting part 32 is fixed around the surface of the positioner 33. The positioner 33 and lower socket 14 are fixed together and never vertically move relative to each other. Namely, the lower socket 14 is firmly attached to the lower part of the thigh just above the knee joint, and the pelvis supporter 20 of the upper socket 12 receives patient's weight, which is surely transferred from the upper socket 12 to the lower socket 14.

Figure 2:
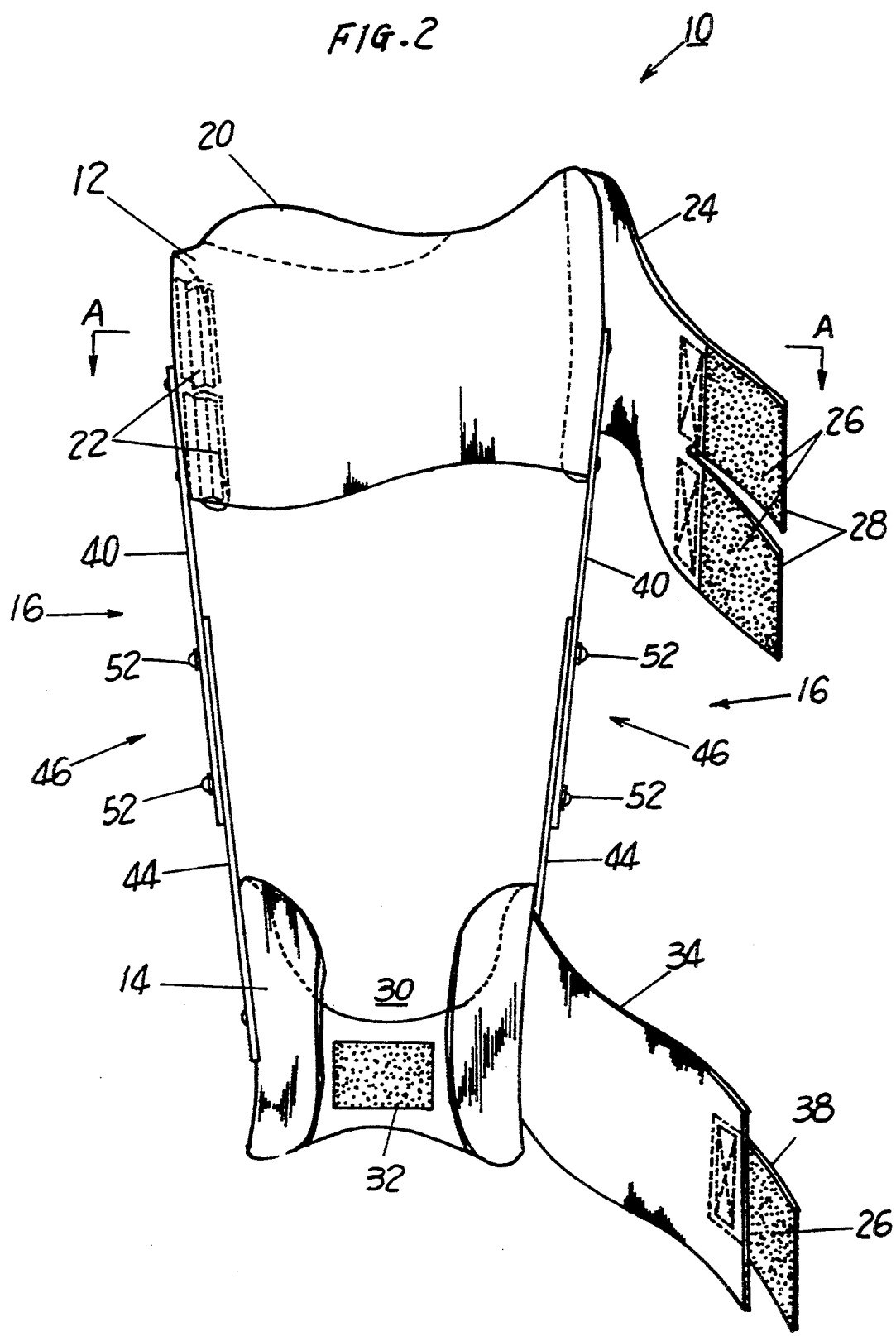
FIG. 2 is a back view of the brace.
Figure 3:
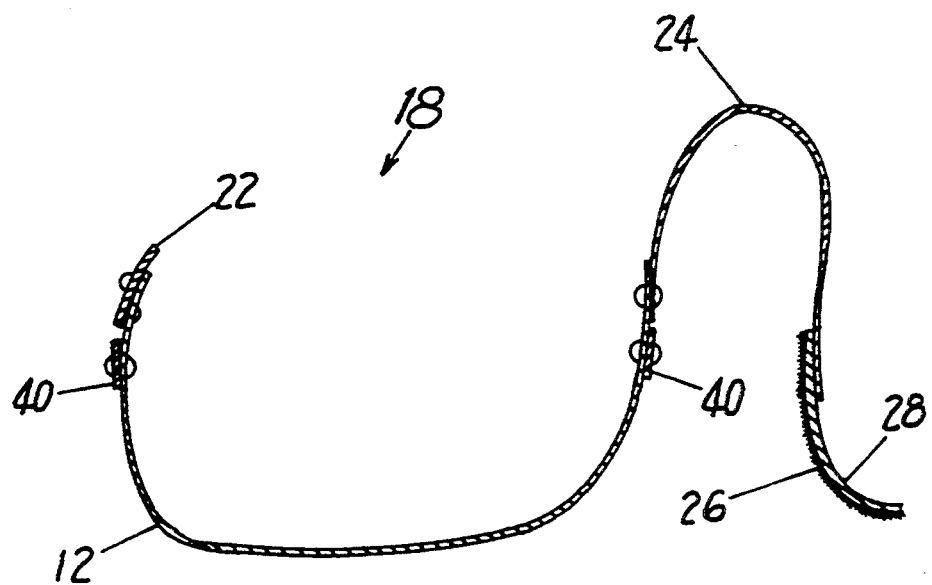
FIG. 3 is a sectional view taken along a line A—A of FIG. 2.

In FIGS. 1 and 2, each side of the lower socket 14 is higher than the central part thereof. An end of the opening 30 is provided with a fastening band 34 made of elastic material. The outer face of the band 34 is rough. The band 34 is sufficiently long to cover and fasten the lower socket 14. A stopper tongue 38 having a velvet fastener 26 is sewn to an end of the band 34.

The lower socket 14 is set from the front of the knee joint and is fixed to the lower periphery of the thigh just above the knee joint. The band 34 is wound over the opening 30, and the velvet fastener 26 of the tongue 38 is removably attached to the surface of the band 34. Consequently, the upper and lower sockets 12 and 14 are easily attached to and detached from the upper and lower parts of the thigh.

The openings 18 and 30 of the upper and lower sockets 12 and 14 are oppositely positioned so that the upper and lower sockets 12 and 14 are attached to the thigh from the opposite sides thereof. Accordingly, the upper and lower sockets 12 and 14 are well-balanced at their positions to firmly hold the thigh.

Figure 5:
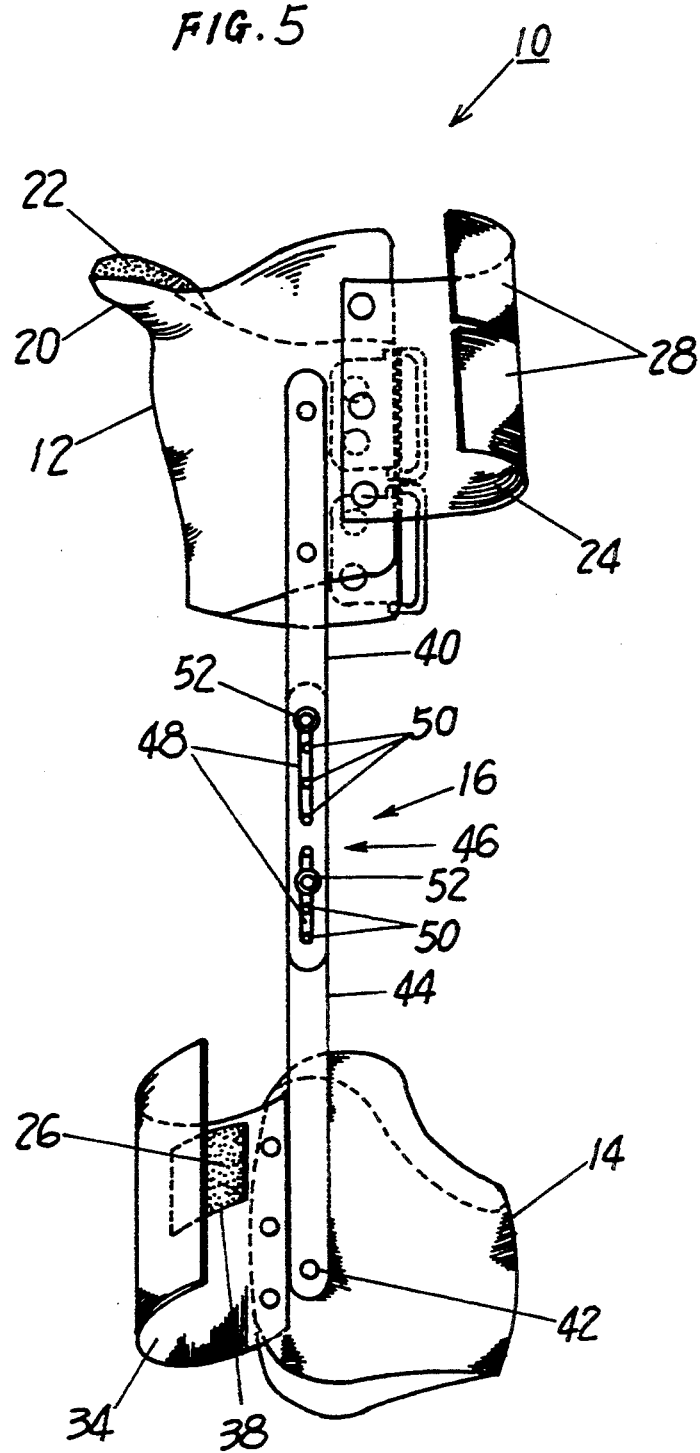
FIG. 5 is a left side view of the brace.

In FIGS. 1, 4, and 5, the sides of the upper and lower sockets 12 and 14 are connected to each other through a pair of left and right connectors 16. Each of the connectors 16 is composed of an upper rod 40 and a lower rod 44 connected to each other. The upper rod 40 has an upper end fixed to the side of the upper socket 12, and the lower rod 44 has a lower end rotatably attached to the side of the lower socket 14 through a pivot 42.

In FIG. 5, each pair of the upper and lower rods 40 and 44 are connected to each other through an adjuster 46. The adjuster 46 involves two long holes 48 formed at a lower end of the upper rod 40, threaded holes 50 formed at an upper end of the lower rod 44, and two screws 52 passed through the long holes 48 and engaged with the threaded holes 50. When the screws 52 are unfastened, the ends of the upper and lower rods 40 and 44 are movable relative to each other within the long holes 48, to adjust a space between the upper and lower sockets 12 and 14 according to the size of the thigh. After the adjustment, the screws 52 are fastened.

The connectors 16 keep a required space between the upper and lower sockets 12 and 14 while supporting the weight of the upper half of the patient. According to the embodiment, the connectors 16 maintain a space K between the upper and lower sockets 12 and 14, and the upper socket 12, connectors 16, and lower socket 14 form a solid structure. Namely, each pair of the upper and lower rods 40 and 44 connected with the adjuster 46 forms a solid linear structure that connects the upper and lower sockets 12 and 14 to each other. Upper ends of the connectors 16 receive the weight of the upper half of the patient wearing the weight bearing brace 10 and directly transfers the weight to lower ends of the connectors 16.

The screws 52 may be unfastened with the patient being laid. Then, the leg can be pulled by a traction unit, to extend thigh muscles.

The adjuster 46 is not limited to the one explained above. Any adjuster is employable if it is capable of adjustably connecting the upper and lower rods 40 and 44 to each other.

The lower rod 44 of each of the connectors 16 is attached to the side of the lower socket 14 through the pivot 42, so that the lower rod 44 and lower socket 14 are rotatable relative to each other around a horizontal axis of the pivot 42. Accordingly, the knee joint with the lower socket 14 is movable with a large degree of freedom.

As explained above, the present invention is characterized in that the upper and lower sockets 12 and 14 are connected to each other through the connectors 16 that adjustably keep a required space between the sockets 12 and 14 while bearing load, and that the upper socket 12 has the pelvis supporter 20.

The pelvis supporter 20 is positioned under the pelvis of the patient when the upper socket 12 is attached to the upper periphery of the thigh of the patient. At the same time, the lower socket 14 is attached to the lower periphery of the thigh. The weight of the upper half of the patient is received by the pelvis supporter 20 and is transferred from the upper socket 12 to the lower socket 14 through the connectors 16, so that the affected hip joint or femur is free from the weight.

In FIGS. 1 to 5, the pelvis supporter 20 is arranged at the central part of the upper end of the upper socket 12. When the brace 10 is attached to the thigh, the pelvis supporter 20 protrudes and curves along the back of the thigh area under the pelvis. The inner wall of the pelvis supporter 20 is provided with an elastic pad 54 such as a sponge pad.

Figure 6:
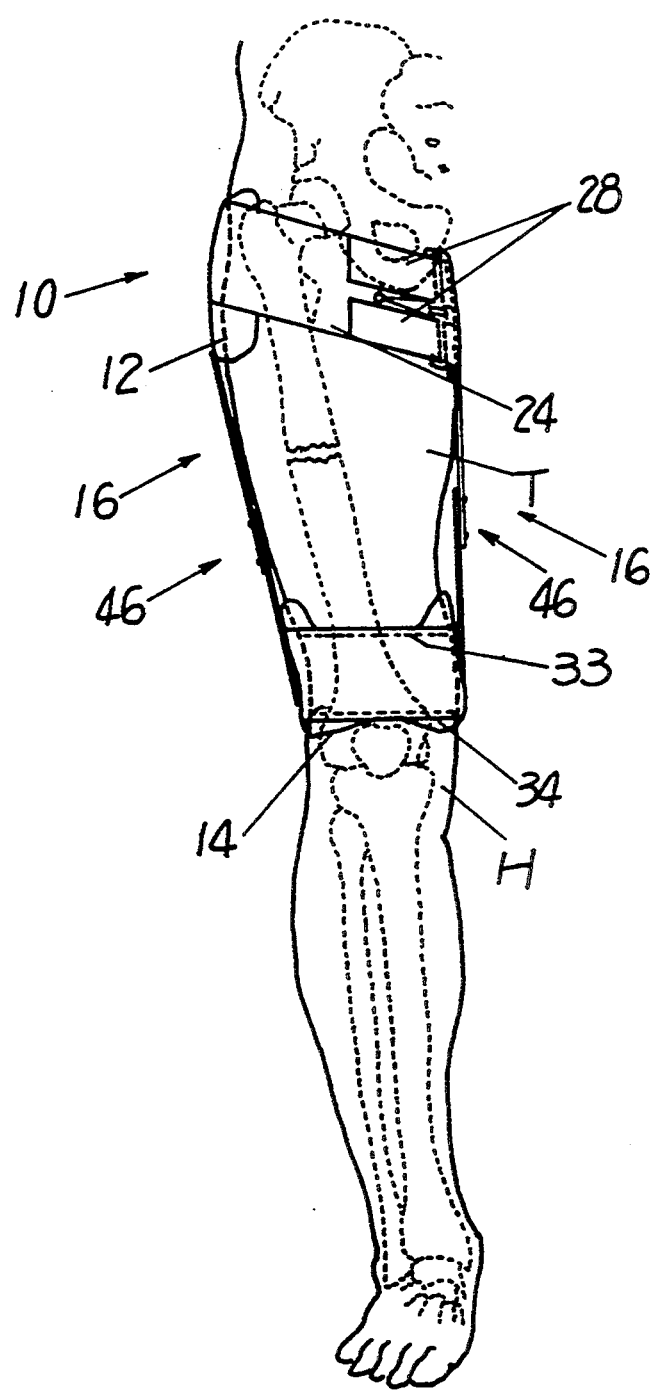
FIG. 6 is a front view showing the right leg of a patient with the brace.
Figure 7:
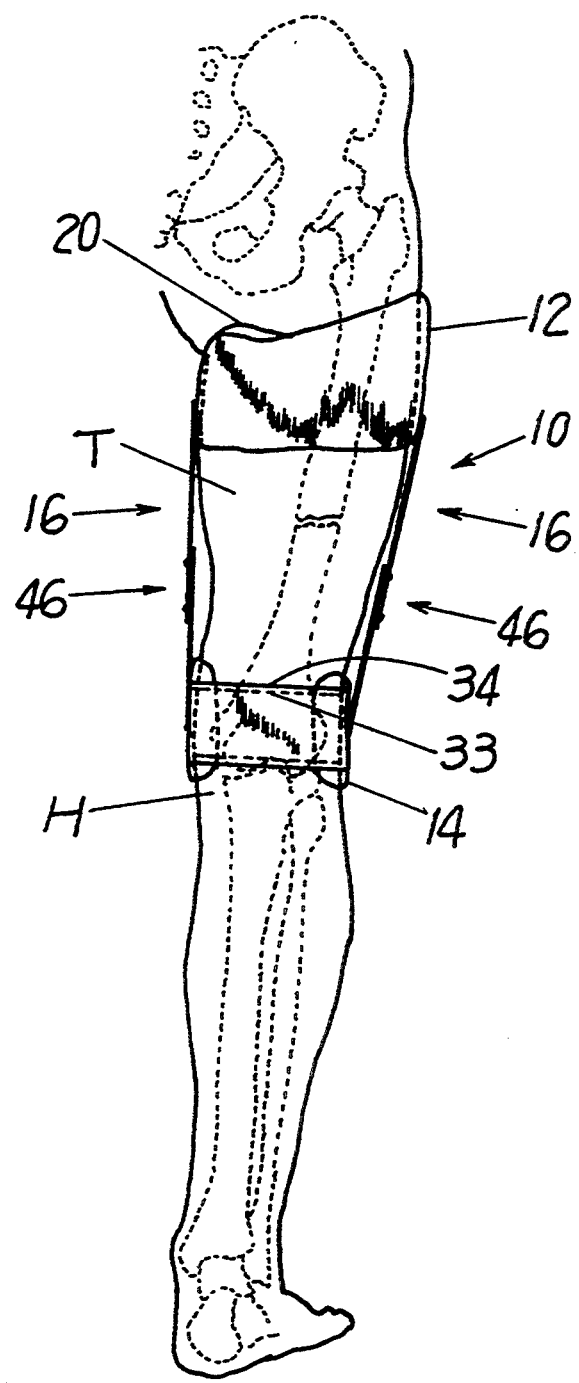
FIG. 7 is a back view showing the leg of FIG. 6.

Operations of the weight bearing brace 10 for a femur and hip joint according to the present invention will be explained with reference mainly to FIGS. 6 to 8.

The adjusters 46 of the connectors 16 are adjusted to determined the positions of the upper and lower rods 40 and 44 of the connectors 16, to properly set the heights of the upper and lower sockets 12 and 14 of the brace 10 for a patient. The pelvis supporter 20 is set under the pelvis of the patient in a way not to prevent the movements of a hip joint. The upper socket 12 is attached to the back of an upper part of a thigh T of the patient. The stopper tongues 28 of the fastening band 24 are stretched over the opening 18, passed through the annular stoppers 22, folded back toward the surface of the band 24, and removably fastened to the surface of the tongues 28.

The lower socket 14 is attached to the front of a lower periphery of the thigh T just above a knee joint H. The fastening band 34 is stretched over the opening 30, and the stopper tongue 38 is removably fixed to the surface of the band 34.

Figure 8:
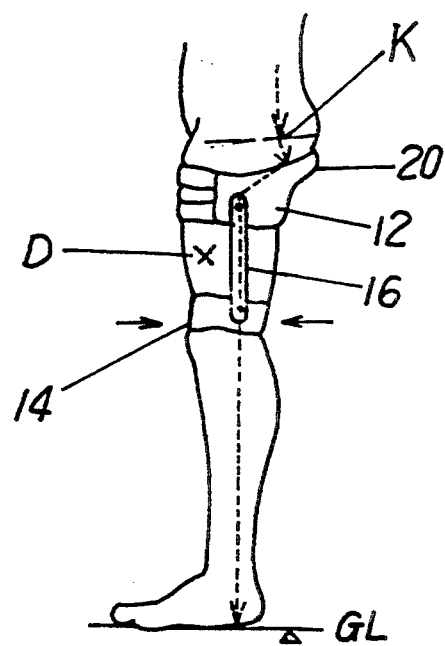
FIG. 8 explains a weight bearing operation of the brace.
Figure 9:
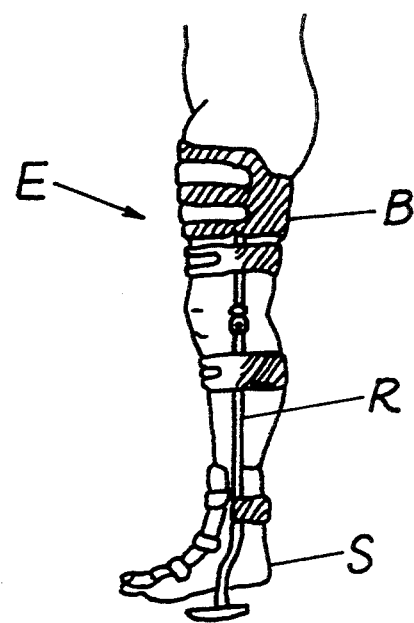
FIG. 9 is a side view showing a weight bearing brace according to a prior art.

In FIG. 8, an affected part D is substantially at the center of the thigh. The weight of the upper half of the patient is supported by the pelvis as indicated with a dotted line M. The weight is received by the pelvis supporter 20 of the upper socket 12 and is transferred to the lower socket 14 through the connectors 16. Since the lower socket 14 is fastened to the sides and upper part of the knee joint H, the weight is transferred to the ground with the knee joint H being freely movable. Accordingly, the femur having the affected part D is substantially free from the weight. In this way, the brace 10 avoids the thigh from receiving the weight, thereby reducing the load onto the hip joint and femur.

As explained above, the weight bearing brace for a femur and hip joint according to the present invention requires no plaster being cast along a leg of a patient. The brace is prepared as a ready-made product, which is always ready to use for every patient. The brace has a simple structure, and therefore, is low cost.

The lower socket 14 of the brace is joined with the connectors 16 to allow a knee joint to freely move. Accordingly, the patient smoothly rehabilitates itself and recovers health.

The brace is composed of a small number of parts, and therefore, has a compact good appearance.

The brace is light to carry and store and is easy to use.

The inner face of the lower socket has the attaching part to be attached to a condyle area above a knee joint. This attaching part stabilizes the brace, and therefore, the lower socket never slips even if patient's weight is applied to the lower socket.

Each of the connectors has the adjuster for adjusting a space between the upper and lower sockets according to the size of a thigh. Accordingly, the brace is applicable for any patient irrespective of the figure of the patient. The space may be adjusted to achieve a traction operation to effectively treat the patient.

The lower socket is rotatably attached to the lower ends of the connectors, to allow a patient to freely move its knee joint. This allows the patient with the brace to walk to rehabilitate itself and spend normal life like a healthy person.

The positioner is arranged around the periphery of a lower part of a thigh, and the periphery of the positioner is fastened by the lower socket, to firmly position the lower socket with respect to the periphery of the lower part of the thigh. The firmly positioned lower socket cooperates with the upper socket, to provide an improved weight bearing effect.

The positioner is made of an annular rubber or synthetic resin material to surely position the lower socket with respect to the periphery of the lower part of the thigh.

We claim:

1. A weight bearing brace for a patient having femur or hip joint trouble, consisting essentially of
    an upper socket removably attachable to the periphery of an upper part of a thigh and provided with a pelvis supporter which is positionable under the pelvis of a patient, said pelvis supporter including a lip protruding outwardly at generally a right angle from said upper socket;
    a lower socket removably attachable to the periphery of a lower part of the thigh to cover the front and sides of the lower periphery of the thigh just above a knee joint;
    connectors for connecting said upper and lower sockets to each other, for bearing a patient's weight, and maintaining a desired space between said upper and lower sockets without bending at any point between said upper and lower sockets;
    so that knee joint itself can move freely while the patient's weight is transferred from the upper socket to the lower socket up to the ground through the connectors.

2. The brace according to claim 1, wherein said lower socket has an inverted U shape in a plan view, and the inner face of said lower socket has an attaching part to be attached to a condyle area above a knee joint.

3. The brace according to any one of claims 2 to 3, wherein said lower socket is rotatably attached to lower ends of said connectors.

4. The brace according to any one of claim 3, further comprising a positioner to be fitted around the periphery of a lower part of the thigh with the periphery of the positioner being fastened with said lower socket, to position said lower socket with respect to the periphery of the lower part of the thigh.

5. The brace according to claim 4, wherein the positioner is made of an annular rubber or synthetic resin material.

6. The brace according to claim 1, wherein each of said connectors has an adjuster for longitudinally extending and shortening said connector.

* * * * *